United States Patent [19]

Robinson et al.

[11] Patent Number: 5,364,396
[45] Date of Patent: Nov. 15, 1994

[54] DISTRACTION METHOD AND APPARATUS

[76] Inventors: Randolph C. Robinson, 7144 S. Chapparal Cir. East, Aurora, Colo. 80016; David A. Hendrick, 4604 Kalispell Way, Aurora, Colo. 80015

[21] Appl. No.: 38,786

[22] Filed: Mar. 29, 1993

[51] Int. Cl.⁵ ............................................. A61F 5/04
[52] U.S. Cl. ...................................... 606/53; 606/54; 606/57; 606/105
[58] Field of Search ....................... 606/53, 54, 55, 56, 606/57, 58, 59, 104, 105, 69, 70, 71

[56] References Cited

U.S. PATENT DOCUMENTS

| | | |
|---|---|---|
| 3,976,060 | 8/1976 | Hildebrandt et al. |
| 4,096,857 | 6/1978 | Cramer et al. |
| 4,244,360 | 1/1981 | Dohogne ............................ 606/56 |
| 4,929,247 | 5/1990 | Rayhack |
| 4,978,348 | 12/1990 | Ilizarov |
| 5,066,224 | 11/1991 | Block et al. |
| 5,129,903 | 7/1992 | Luhr et al. ............................ 606/69 |

Primary Examiner—Stephen C. Pellegrino
Assistant Examiner—Sonja C. Harris
Attorney, Agent, or Firm—Fields, Lewis, Pittenger, Rost & Smith

[57] ABSTRACT

An implantable bone distraction device and method of using the device are disclosed. The device includes spaced first and second low profile blocks for subcutaneous implantation and attachment to osteotomically separated bone sections. The first block defines a drive chamber bore while the second block defines a threaded bore. A rotatable drive rod having a first end is received in the drive chamber bore of the first block. The rotatable drive rod's other end is threadably received in the threaded bore of the second block. The device further includes drive rod actuator located in the drive chamber bore for cooperating with the first end of the drive rod to rotate the drive rod so that one can adjust the depth to which the rod's threaded end is received in the threaded bore of the second block. This enables one to adjust the spacing between the first and second blocks, thereby enabling one to controllably distract the separated bone sections to enhance bone growth therebetween.

9 Claims, 2 Drawing Sheets

DISTRACTION METHOD AND APPARATUS

TECHNICAL FIELD OF THE INVENTION

The invention relates generally to devices designed to distract bone sections separated by an osteotomy, i.e. a fracture or cut. More particularly, the invention relates to implantable distraction devices which are capable of being gradually adjusted to controllably distract osteotomically separated bone sections for the purpose of enhancing bone growth between the sections.

BACKGROUND OF THE INVENTION

The prior art contains many bone distraction devices which permit bone lengthening by cutting the bone and distracting the ends of a bone apart by a desired distance, affixing the ends in place with a permanent or temporary internal splint and filling the gap between the bone ends with a bone segment to facilitate growth across the gap. Devices of this type are disclosed in U.S. Pat. Nos. 4,929,247 to Rayhack; 3,244,170; 3,604,414; 4,475,546; 4,187,841; 3,709,219; and 2,333,033.

Most of the foregoing distraction devices do not provide for gradual distraction of the bones. In fact, most of these devices permit bone distraction only for the purpose of inserting a bone segment in the gap between the distracted bone ends. These devices then compress the bone sections to prevent the bone segment inserted therebetween from falling or slipping out the gap.

U.S. Pat. Nos. 4,096,857 to Kramer, et al., and 3,976,060 to Hildebrant, et al. disclose implantable distraction devices which permit gradual bone distraction between osteotomically separated bone sections. The Hildebrant patent discloses a number of devices having sealed housings, each of which has an extension means and power drive means for extending the extension means to distract separated bone sections. Hildebrant further discloses that the power drive means may be controlled by a control means such as electronic control circuitry which may be actuated externally by a magnetic field located outside the device's housing, even outside the patient's body.

Notwithstanding the achievements of the prior art devices, a need still exists for an implantable distraction device which provides or is capable of the following: (1) providing gradual distraction between osteotomically separated bone sections, (2) easily implanted and attached to a patient's osteotomically separated bone sections, (3) has an extremely low profile so that it is not easily detected even though it may be subcutaneously located just under the skin, (4) economically constructed using a minimal number of parts, and (5) structurally stable when anchored to bone so that the occurrence of flexural moments is minimized between the device's points of attachment to the osteotomically separated bone sections.

DISCLOSURE OF THE INVENTION

The foregoing needs are addressed by the implantable bone distraction device of the present invention. The device includes spaced first and second low profile blocks also referred to herein as block means for subcutaneous implantation and attachment to osteotomically separated bone surfaces. The first block or block means defines a drive chamber bore and the second block or block means defines a threaded bore. A rotatable drive rod having a first drive end is received in the drive chamber bore of the first block while rotatable drive rod's other end, i.e. its distal end, is threadably received in the threaded bore of the second block or block means.

The device further includes drive rod actuation means located in the drive chamber bore for cooperating with the first drive end of the drive rod to rotate the drive rod so that one can adjust the depth to which the rod's threaded distal end is threadably received in the threaded bore of the second block or block means. By adjusting this depth, one can adjust the spacing between the first and second blocks which enables one to controllably distract the separated bone sections to enhance bone growth between the sections.

In a preferred embodiment, the distraction device of the present invention further includes guide pin means, preferably a pair of guide pins, for maintaining the first and second blocks in alignment with each other as the spacing between the blocks is adjusted. The guide pins have a first end which is rigidly attached to the first block and a second end which is slidably received in complementarily shaped bores defined in the second block. The longitudinal axis of each guide pin is also preferably parallel to that of the rotatable drive rod so that the first and second blocks can be maintained in alignment with each other as spacing therebetween is adjusted.

In a further embodiment of the present invention, first and second attachment plates are provided for respectively attaching the first and second block means to the bone surfaces. Each plate has a central section which is rigidly attached to the underside surface of its respective block. Each plate also defines at least one, preferably several, outwardly projecting sections which extend beyond the perimeter of the block to which it is attached. Each outwardly projecting section defines at least one screw hole for receiving a bone screw to secure the plate and thus the block to its respective bone section.

In yet a further embodiment of the invention, the bone distraction device includes a percutaneous port projecting outwardly from the first block which is capable of extending through the skin of a patient. The port defines a bore in communication with the drive chamber bore of the first block for receiving an adjustment tool which cooperates with the drive rod actuation means to rotate the drive rod so that spacing between the first and second blocks can be adjusted to control distraction between the bone sections and thus enhance bone growth therebetween.

BRIEF DESCRIPTION OF THE DRAWINGS

The invention will be more readily understood by reference to the accompanying drawings wherein like reference numerals indicate like elements throughout the drawing figures, and in which.

DETAILED DESCRIPTION OF THE INVENTION

FIGS. 2 through 6 illustrate an implantable bone distraction device 10 of the present invention for distracting osteotomically separated bone sections 12 and 14 of a patient's skull. Device 10 enables control over the distraction process, i.e. gradual distraction, thereby making it possible to enhance bone growth between skull sections 12 and 14.

As best illustrated in FIGS. 3 through 6, device 10 generally includes a first and second low profile block means 16 and 18, respectfully, which are also referred to herein as blocks 16, 18. Blocks 16 and 18 are designed for subcutaneous implantation and attachment to osteotomically separated bone sections such as bone skull sections 12 and 14 illustrated in FIG. 2.

Figure 3:
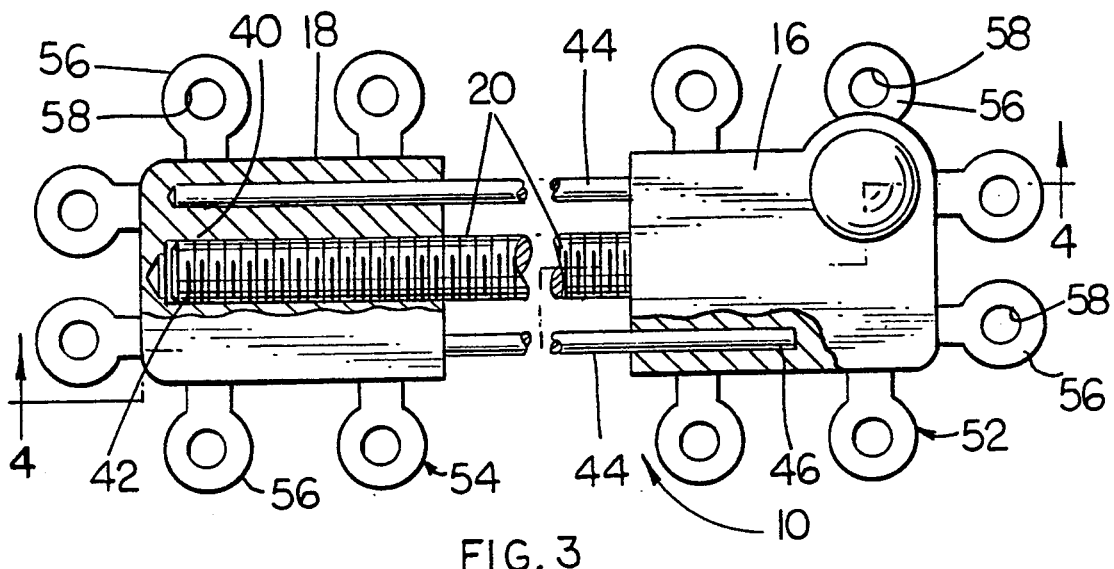
FIG. 3 is a top plan view partially cut away showing one of the distraction devices illustrated in FIG. 2.
Figure 4:
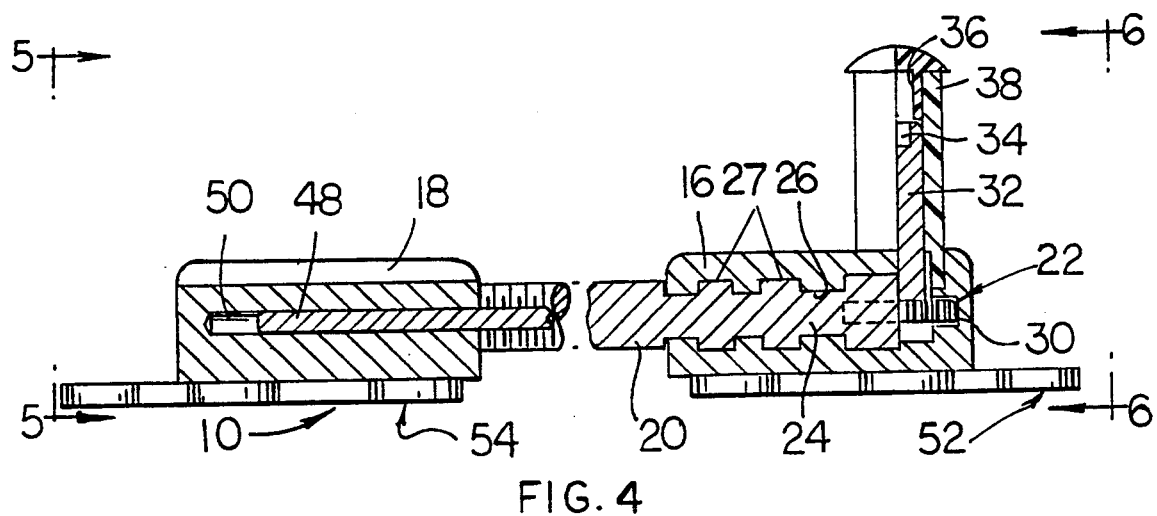
FIG. 4 is a partially cut away side view of the device illustrated in FIG. 3 taken along lines 4—4 of FIG. 3.
Figure 5:
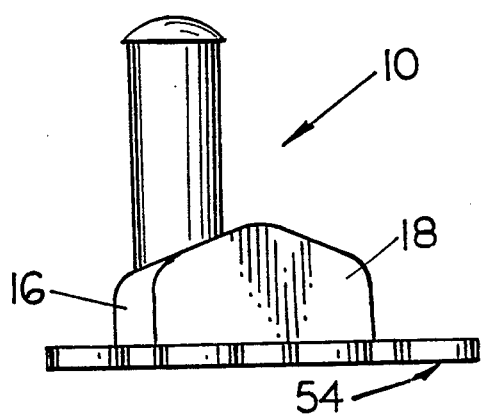
FIG. 5 is an end elevation view taken along lines 5—5 of FIG. 4.
Figure 6:
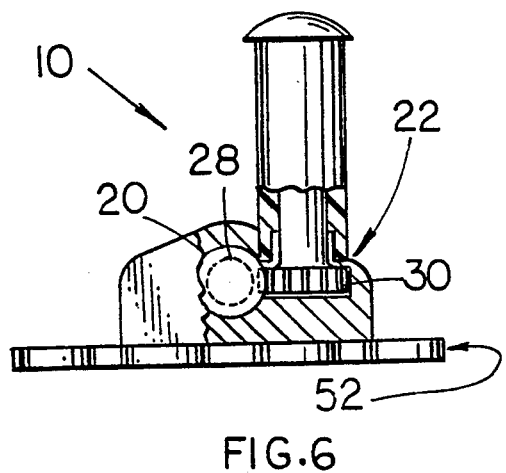
FIG. 6 is a partially cut away end elevation view taken along lines 6—6 of FIG. 4.

As best illustrated in FIG. 4, blocks 16, 18 have an extremely low profile, i.e. height so that they will be difficult to detect even when implanted just under the skin. In a preferred embodiment, the low profile of blocks 16, 18 is such that their height is less than their width as illustrated in FIGS. 5 and 6, and their length as illustrated in FIGS. 3 and 4. Device 10 also generally includes a rotatable drive rod 20 and drive rod actuation means 22 for cooperating with drive rod 20 to rotate the drive rod so that the spacing between first and second blocks 16 and 18 can be adjusted. Device 10 may also include means for sealing the various penetrations of the first and second blocks 16 and 18, such as the drive rod bore and the threaded bore, to prevent fouling of internal moveable components by tissues or fluid external to the blocks 16 and 18. Such a seal might include a silicon sleeve or other means familiar to those skill in the mechanical arts.

Turning now to the details of device 10 as best illustrated in FIGS. 3, 4 and 6, drive rod 20 has an end 24 which is received in a drive chamber bore 26 defined by first block 16. As also illustrated, end 24 is provided with a pair of cylindrically shaped collars 27 which are preferably integral with end 24. As also illustrated, each collar 27 is received within a complementarily shaped portion (not numbered) of the drive chamber bore to retain drive rod 20 in the chamber bore. The diameters of collars 27 are slightly smaller than their complementary shaped bore portions to permit rotation of drive rod 20.

FIGS. 4 and 6 illustrate that device 10 utilizes a worm gear type drive rod actuation means which is provided by contouring the end surface 28 of end 24 so that it has a helical worm-like shape (not shown). This type of shaped device is generally referred to as a worm by those skilled in the mechanical arts. Worm shaped end surface 28 (or worm 28 also used herein) (not shown) cooperates with a worm wheel 30 which is mounted on the end of a shaft 32 and coaxially aligned therewith. The other end (not numbered) of shaft 32 is provided with a notched portion 34 for receiving the end of an adjustment tool or wrench (not shown) such as an allen wrench which when inserted into notch 34, enables one to rotate shaft 32 and worm wheel 30 which, in turn, drives or rotates the drive rod 20 via worm 28.

As illustrated in FIG. 4, shaft 32 is received within a bore 36 of a port 38 which is designed and provided with a height so that it is capable of extending through patient's skin (i.e. when device 10 is attached to bone sections such as sections 12, 14). This enables the insertion of a wrench or other suitable tool into notch 34 to adjust the spacing between blocks 16, 18 and thus control the distraction process.

While the illustrated worm gear type actuation means is the preferred means for actuating rotation of the drive rod, other means for actuating rotation of the drive means are considered to be within the scope of the present invention. Other suitable actuation means include the following: (1) a simple hydraulic motor, in lieu of the worm gear arrangement, driven by a remote hydraulic power source via a narrow hydraulic line to the drive block; (2) a simple mechanical ratchet mechanism in lieu of the worm gear arrangement driven by a remote mechanical force via a narrow mechanical cable to the drive block. It is also contemplated that the motive forces for hydraulically or mechanically actuating the rotating drive rod could be supplied by a small solenoid type motor which could be used to actuate rotation of the drive rod. Such a motor could be remotely controlled with conventional electronic circuitry by a remote control device external to the patient's body. It will be appreciated that a remotely controlled device would not need shaft 32 or port 38 for receiving the aforementioned adjustment tool or wrench, and thus, would be fully implantable. A fully implantable device would be useful in attaching the device to bone surfaces which are not located near skin or on bone surfaces that do not face the skin.

Turning now to block 18, it can be seen in FIGS. 3 and 4 that block 18 defines a threaded bore 40 for receiving a threaded end 42 of drive rod 20. Those skilled in the art will appreciate that by rotating drive rod 20, (i.e. by rotating shaft 32 via worm gear arrangement as described above), one can adjust the depth to which threaded end 42 is received within threaded bore 40. This, it will be appreciated, adjusts the spacing between blocks 16 and 18, thereby enabling one to control the distraction process, as previously discussed.

FIGS. 3 and 4 also illustrate that device 10 is provided with a pair of guide pins 44, having ends 46 and 48. Ends 46 are received in complementarily shaped bores (not numbered) so that they are rigidly affixed to first block 16. Ends 48 are slideably received in bores 50 of block 18 so that they are capable of slidable movement therein. As such, it will be appreciated that ends 48 slide within bores 50 as one adjusts the depth to which rod 20 is received within threaded bore 40.

Guide pins 44 serve to maintain first and second blocks 16, 18 aligned with each other as the spacing between the blocks is adjusted. In addition, the guide pins enhance the structural stability of device 10 when it is anchored to osteotomically segmented bone sections, thereby minimizing the occurrence of fluctural moments between the device's points of attachment to the separated bone sections.

FIGS. 2 through 6 also illustrate that device 10 is provided with attachment plates 52, 54 for respectively attaching blocks 16 and 18 to osteotomically separated bone sections 12, 14. The means for attaching the attachment plates to the underside surface of blocks 16 and 18 is not shown. However, the plates, i.e. their central sections (not numbered) can be secured to the block's underside with screws or they can be welded thereto.

FIG. 3 illustrates that each plate 52, 54 is also provided with a plurality, six as illustrated, of outwardly projecting sections or eyelets 56, each of which defines a screw hole 58 for receiving a bone screw 59 to secure the plate and its attached block against the surface of a bone section. Plates 52, 54 are preferably made out of a malleable metal such as titanium so that the plate can be conformed or bent to the shape of the bone surface. Stainless steel may also be used if more rigidity is needed, e.g. in long bones or the mandible.

Figure 1:
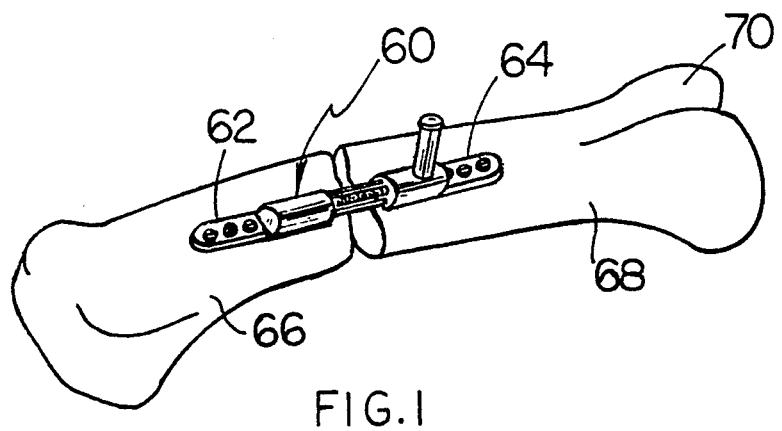
FIG. 1 is a perspective view of a distraction device of an embodiment of the present invention which illustrates the device attached to osteotomically separated bone sections of a long bone.
Figure 2:
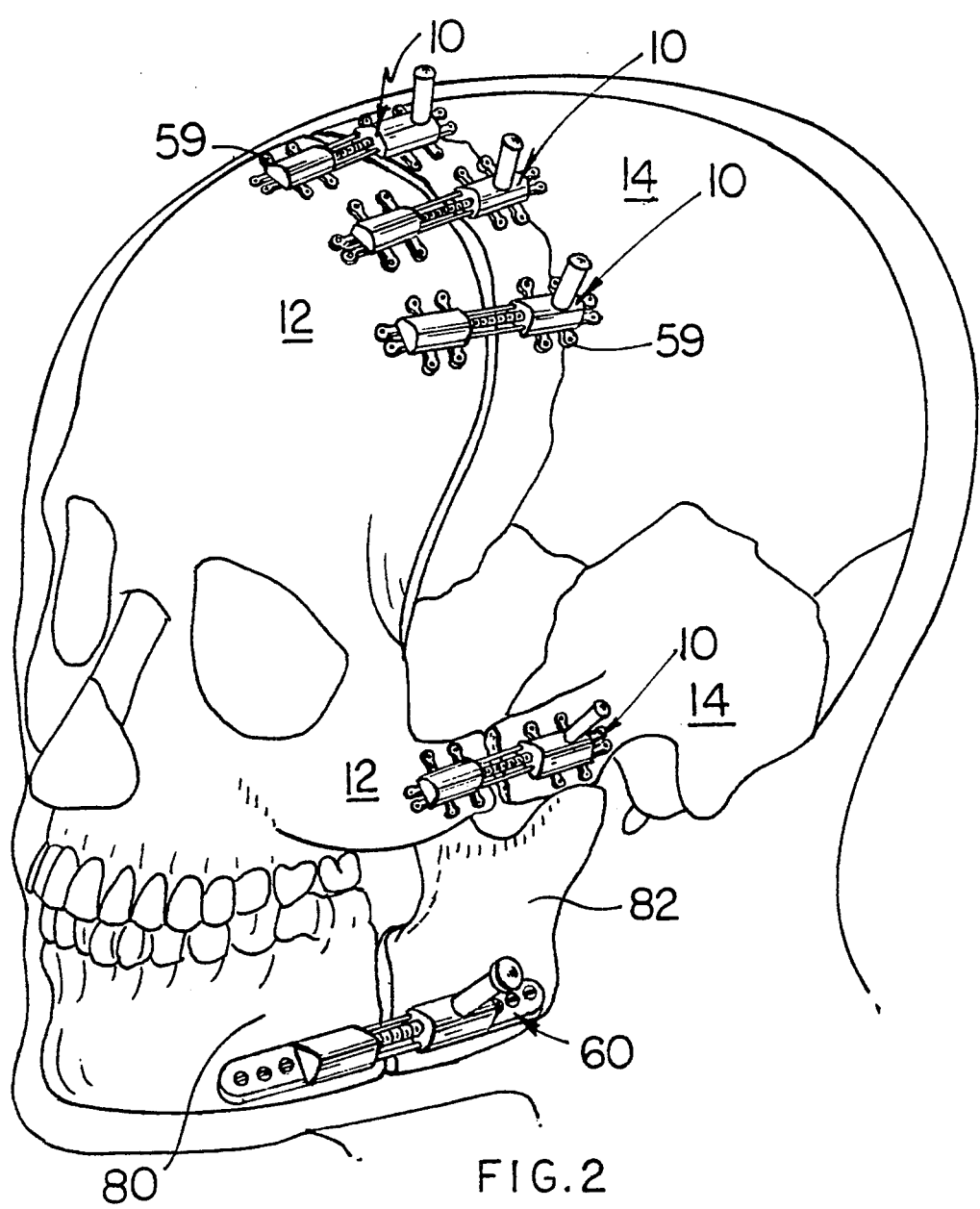
FIG. 2 illustrates the device of FIG. 1 attached to osteotomically separated sections of the mandible and another distraction device of the present invention attached to osteotomically separated sections of a person's skull and zygoma.

FIGS. 1 and 2 illustrate another distraction device 60 of the present invention which is identical to device 10 with the exception that it is provided with differently shaped attachment plates 62, 64 for attaching or anchoring the device to differently shaped bone sections. FIG. 1 illustrates device 60 attached to osteotomically separated sections 66, 68 of a long bone 70. FIG. 2 illustrates device 60 attached to osteotomically separated bone sections 80 and 82 of the mandible.

From the foregoing description, those skilled in the art will appreciate that the present invention provides an implantable distraction device which not only enables gradual distraction but is easily implanted and attached to osteotomically separated bone sections as well. It will be appreciated that the device has an extremely low profile so that it will not be easily detected even though it may be subcutaneously located just under the skin. It will also be appreciated that the device is easily manufactured and assembled since it has only a few parts. In addition, it will be appreciated that the device, when anchored to bone sections, is structurally stable, thereby minimizing the occurrence of fluctural moments between the device's points of attachment to osteotomically separated bone sections.

The invention has been described in detail with reference to particular embodiments thereof, but it will be understood that various other modifications can be effected within the spirit and scope of this invention.

What is claimed is:

1. An implantable bone distraction device for distracting osteotomically separated bone sections, said bone distraction device comprising:
   first low profile block means for subcutaneous implantation and attachment to a first bone section, said first block means defining a drive chamber bore;
   second low profile block means spaced from said first low profile block means for subcutaneous implantation and attachment to a second bone section separated from the first bone section by an osteotomy located between the bone sections, said second block also defining a threaded bore;
   a rotatable drive rod having a first drive end received in said drive chamber bore of said first block means and a threaded distal end threadably received in said threaded bore of said second block means;
   drive rod actuation means located in said drive chamber bore for cooperating with said first drive end of said drive rod to rotate said drive rod so that the inherent depth to which said rod's threaded distal end is threadably received within said threaded bore can be adjusted, the adjustment of which adjusts the spacing between the first and section block means which enables distraction between the first and second bone sections to be controlled so that bone growth therebetween can be enhanced;
   a percutaneous adjusting port projecting outwardly from said first block means and being rigidly connected thereto, said percutaneous adjusting port defining a bore in communication with said drive chamber bore of said first block means; and
   an adjustment tool for receipt in said bore of said percutaneous adjusting port and for cooperating with said drive rod actuation means to rotate said drive rod so that the spacing between the first and second bone block means can be adjusted to enhance bone growth.

2. An implantable bone distraction device as claimed in claim 1 wherein said drive rod actuation means includes a worm gear.

3. An implantable bone distraction device as claimed in claim 2 further comprising a collar rigidly attached to the first drive end of said drive rod for receipt in a complementarily shaped portion of said drive chamber bore, said collar received in said portion serving to retain said drive rod in said drive chamber bore and yet permit said drive rod to rotate therein.

4. An implantable bone distraction device for distracting osteotomically separated bone sections, said bone distraction device comprising:
   first low profile block means for subcutaneous implantation and attachment to a first bone section, said first block means defining a drive chamber bore;
   second low profile block means spaced from said first low profile block means for subcutaneous implantation and attachment to a second bone section separated from the first bone section by an osteotomy located between the bone sections, said second block also defining a threaded bore;
   a rotatable drive rod having a first drive end received in said drive chamber bore of said first block means and a threaded distal end threadably received in said threaded bore of said second block means;
   drive rod actuation means located in said drive chamber bore for cooperating with said first drive end of said drive rod to rotate said drive rod so that the inherent depth to which said rod's threaded distal end is threadably received within said threaded bore can be adjusted, the adjustment of which adjusts the spacing between the first and section block means which enables distraction between the first and second bone sections to be controlled so that bone growth therebetween can be enhanced;
   a first and second attachment plate for respective attachment to said first and second block means, each attachment plate having a central section which is rigidly attached to an underside surface of its respective block means, each plate also defining at least one outwardly projecting section projecting outwardly from the block means to which it is attached, said outwardly projecting section defining at least one screw hole for receiving a bone screw to secure said plate and block means attached thereto to a bone section; and
   wherein the longitudinal axes of said drive rod and said first and second guide pins lie in a common plane.

5. An implantable bone distraction device for distracting osteotomically separated bone sections, said bone distraction device comprising:
   first low profile block means for subcutaneous implantation and attachment to a first bone surface, said first block means defining a drive chamber bore;

second low profile block means spaced from said first low profile block means for subcutaneous implantation and attachment to a second bone section separated from the first bone section by an osteotomy located between the bone sections, said second block also defining a threaded bore, said first and second low profile block means also having a height, length and width wherein the height of each block means is less than its width and length;

a rotatable drive rod having a first drive end received in said drive chamber bore of said first block means and a threaded distal end threadably received in said threaded bore of said second block means; and drive rod actuation means located in said drive chamber bore for cooperating with said first drive end of said drive rod to rotate said drive rod so that the inherent depth to which said rod's threaded distal end is threadably received within said threaded bore can be adjusted, the adjustment of which adjusts the spacing between the first and section block means which enables distraction between the first and second bone sections to be controlled so that bone growth therebetween can be enhanced.

6. An implantable bone distraction device for distracting osteotomically separated bone sections, said bone distraction device comprising:

first low profile block means for subcutaneous implantation and attachment to a first bone section, said first block means defining a drive chamber bore;

second low profile block means spaced from said first low profile block means for subcutaneous implantation and attachment to a second bone section separated from the first bone section by an osteotomy located between the bone sections, said second block also defining a threaded bore;

a rotatable drive rod having a first drive end received in said drive chamber bore of said first block means and a threaded distal end threadably received in said threaded bore of said second block means;

drive rod actuation means located in said drive chamber bore for cooperating with said first drive end of said drive rod to rotate said drive rod so that the inherent depth to which said rod's threaded distal end is threadably received within said threaded bore can be adjusted, the adjustment of which adjusts the spacing between the first and section block means which enables distraction between the first and second bone sections to be controlled so that bone growth therebetween can be enhanced; and remote control means for remotely controlling said drive rod actuation means so that spacing between said first and second block means can be externally adjusted.

7. An implantable bone distraction device for distracting osteotomically separated bone sections, said bone distraction device comprising:

first low profile block means for subcutaneous implantation and attachment to a first bone section, said first block means defining a drive chamber bore;

second low profile block means spaced from said first low profile block means for subcutaneous implantation and attachment to a second bone section separated from the first bone section by an osteotomy located between the bone sections, said second block also defining a threaded bore;

a rotatable drive rod having a first drive end received in said drive chamber bore of said first block means and a threaded distal end threadably received in said threaded bore of said second block means;

drive rod actuation means located in said drive chamber bore for cooperating with said first drive end of said drive rod to rotate said drive rod so that the inherent depth to which said rod's threaded distal end is threadably received within said threaded bore can be adjusted, the adjustment of which adjusts the spacing between the first and section block means which enables distraction between the first and second bone sections to be controlled so that bone growth therebetween can be enhanced; and means for sealing said drive chamber bore to prevent body fluids from contacting said drive rod actuation means.

8. An implantable bone distraction device for distracting osteotomically separated bone sections, said bone distraction device comprising:

first low profile block means for subcutaneous implantation and attachment to a first bone section, said first block means defining a drive chamber bore;

second low profile block means spaced from said first low profile block means for subcutaneous implantation and attachment to a second bone section separated from the first bone section by an osteotomy located between the bone sections, said second block also defining a threaded bore;

a rotatable drive rod having a first drive end received in said drive chamber bore of said first block means and a threaded distal end threadably received in said threaded bore of said second block means;

drive rod actuation means located in said drive chamber bore for cooperating with said first drive end of said drive rod to rotate said drive rod so that the depth to which said rod's threaded distal end is threadably received within said threaded bore can be adjusted, the adjustment of which adjusts the spacing between the first and section block means which enables distraction between the first and second bone sections to be controlled so that bone growth therebetween can be enhanced; and means for sealing said threaded bore to prevent body fluids from contacting said drive rod's threaded distal end received in said threaded bore.

9. A method for controllably distracting osteotomically separated bone sections, said method comprising:

providing an implantable bone distraction device for distracting osteotomically separated bone sections, the bone distraction device including:

first low profile block means for subcutaneous implantation and attachment to a first bone surface, the first block means defining a drive chamber bore;

second low profile block means spaced from said first low profile block means for subcutaneous implantation and attachment to a second bone section, the second bone section being separated from the first bone section by an osteotomy located between the bone sections, the second block also defining a threaded bore;

a rotatable drive rod having a first drive end received in said drive chamber bore of the first block means and a threaded end threadably received in the threaded bore of the second block means; and drive rod actuation means located in said drive chamber bore for cooperating with the first drive end of the drive rod to rotate the drive rod so that the depth to which the rod's threaded distal end is threadably received within the threaded bore can be adjusted, the adjustment of which adjusts the spacing between the first and section block means which enables distraction between the first and second bone sections to be controlled so that bone growth therebetween can be enhanced;

implanting the distraction device in a patient's body so that the first low profile block means is attached to a first bone surface and the second low profile block means is attached to a second bone section osteotomically separated from the first bone section; and controllably actuating the drive rod actuation means to rotate the drive rod a predetermined amount to adjust spacing between the blocks so that bone growth therebetween is enhanced.

* * * * *